(12) United States Patent
Michalski et al.

(10) Patent No.: US 8,205,512 B1
(45) Date of Patent: Jun. 26, 2012

(54) SYSTEMS AND METHODS FOR COLLECTION AND DETECTION OF PARTICULATES IN THE AIR

(75) Inventors: Jeffrey Charles Michalski, Austin, TX (US); Matthew Tant Richardson, Austin, TX (US); Michael Joseph Foley, Austin, TX (US)

(73) Assignee: Airogistic, L.L.P, Austin, TX (US)

( * ) Notice: Subject to any disclaimer, the term of this patent is extended or adjusted under 35 U.S.C. 154(b) by 743 days.

(21) Appl. No.: 12/228,899

(22) Filed: Aug. 15, 2008

Related U.S. Application Data

(60) Provisional application No. 60/964,983, filed on Aug. 16, 2007.

(51) Int. Cl.
*G01N 1/20* (2006.01)

(52) U.S. Cl. ............ 73/863.56; 73/863.57; 73/863.61; 73/863.41

(58) Field of Classification Search ............ 73/863.56, 73/863.57, 863.86, 28.04, 863.41, 863.61
See application file for complete search history.

(56) References Cited

U.S. PATENT DOCUMENTS

| | | | | |
|---|---|---|---|---|
| 3,938,367 A * | 2/1976 | Fletcher et al. | ............ | 73/863.22 |
| 4,926,679 A * | 5/1990 | Dewhurst | ............ | 73/28.05 |
| 5,626,651 A * | 5/1997 | Dullien | ............ | 95/214 |
| 6,217,636 B1 | 4/2001 | McFarland | | |
| 6,376,732 B1 | 4/2002 | Ngan | | |
| 6,508,864 B2 | 1/2003 | Day | | |
| 6,688,187 B1 | 2/2004 | Masquelier | | |
| 7,123,826 B2 * | 10/2006 | Belcher | ............ | 392/478 |
| 7,125,437 B2 | 10/2006 | Bryden et al. | | |
| 2004/0247401 A1 * | 12/2004 | Witheridge | ............ | 406/122 |
| 2005/0005711 A1 * | 1/2005 | Gysling et al. | ............ | 73/861.08 |
| 2006/0169064 A1 * | 8/2006 | Anschutz et al. | ............ | 73/863.21 |
| 2009/0036288 A1 | 2/2009 | Hu et al. | | |

OTHER PUBLICATIONS

Brandon Wayne Moncla, A Study of Bioaerosol Sampling Cyclones, a thesis, Dec. 2004.
Manpreet Singh Phull, An Improved Wetted-Wall Bioaerosol Sampling Cyclone, a thesis, Aug. 2005.

* cited by examiner

*Primary Examiner* — Hezron E Williams
*Assistant Examiner* — Paul West
(74) *Attorney, Agent, or Firm* — Christopher & Weisberg, P.A.

(57) ABSTRACT

Embodiments include systems and methods for collection and identification of particulates in the air. In one embodiment, two different path ways are provided from a single adjustable inlet: one for collection and one for detection. A removable insert positionable within a collection tube enables a user to switch between the collection mode and the detection mode. This embodiment captures both the physical mechanisms of switching the air flow paths as well as sequencing of controls and valves and regulation or changing the air flow rate in the different modes of operation. This and other embodiments are disclosed herein.

20 Claims, 13 Drawing Sheets

Figure 1:
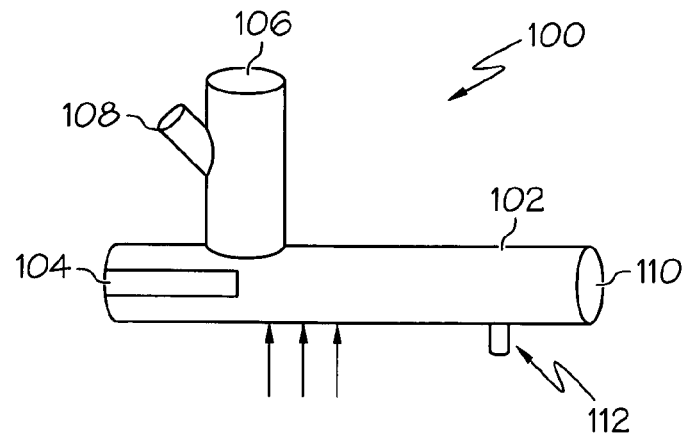
Figure 2:
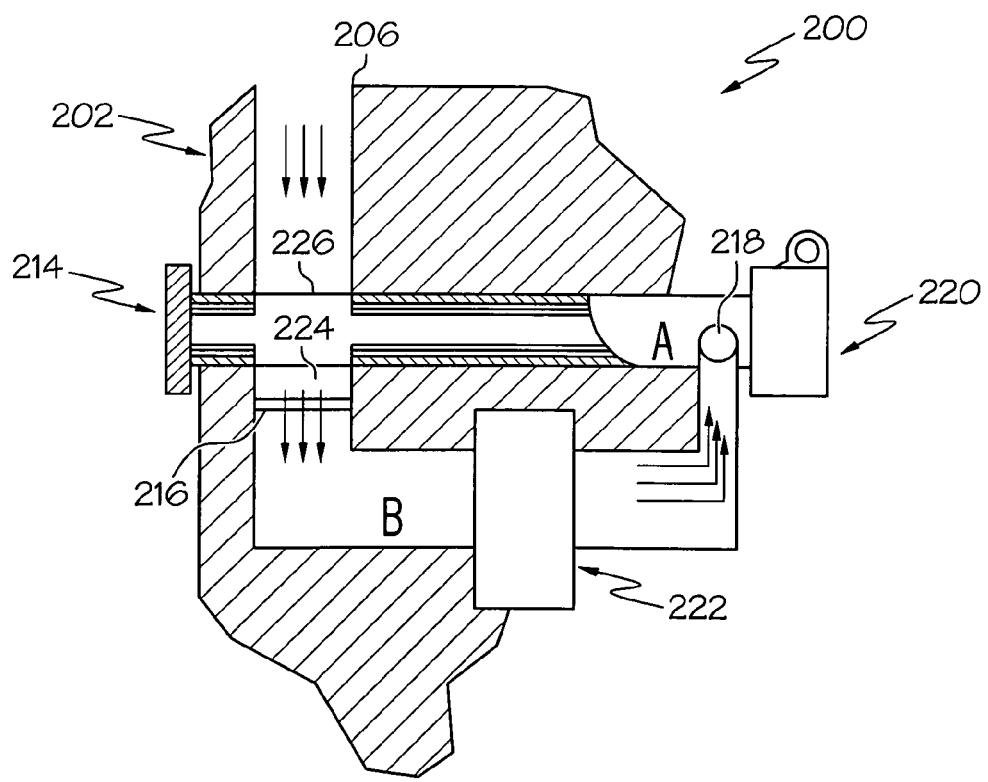
Figure 3D:
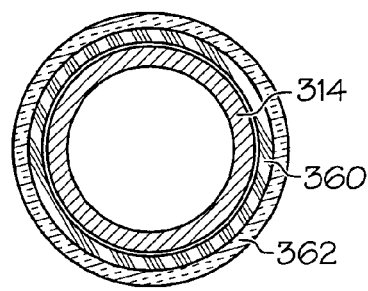
Figure 3E:
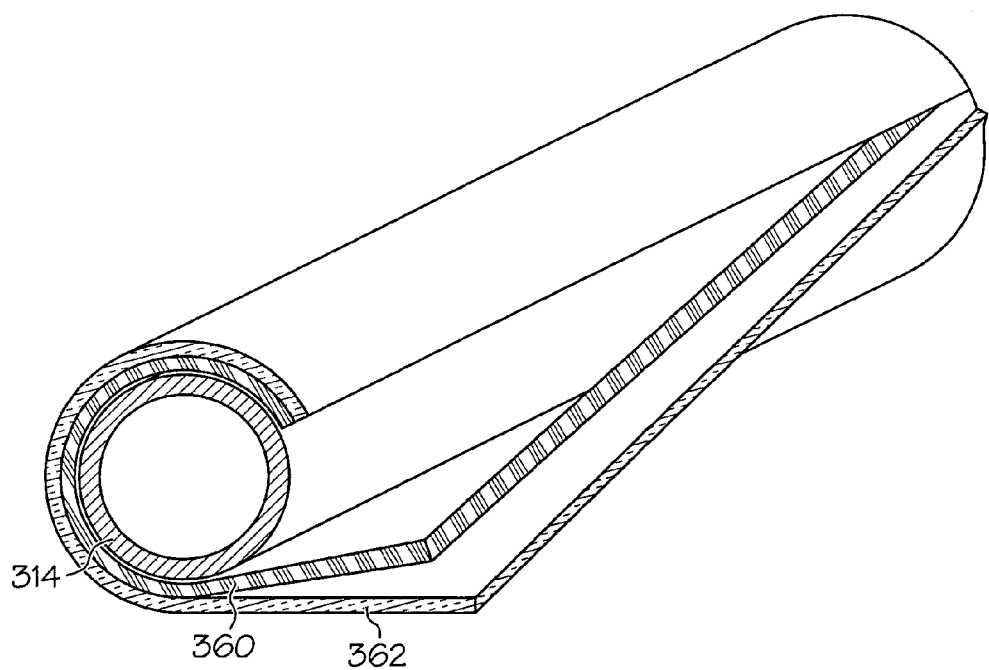
Figure 4A:
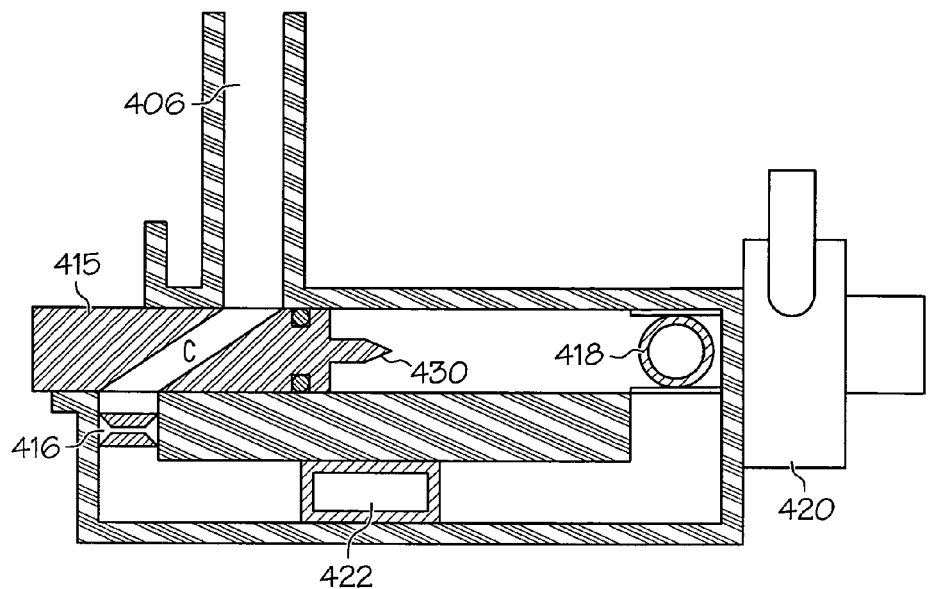
Figure 4B:
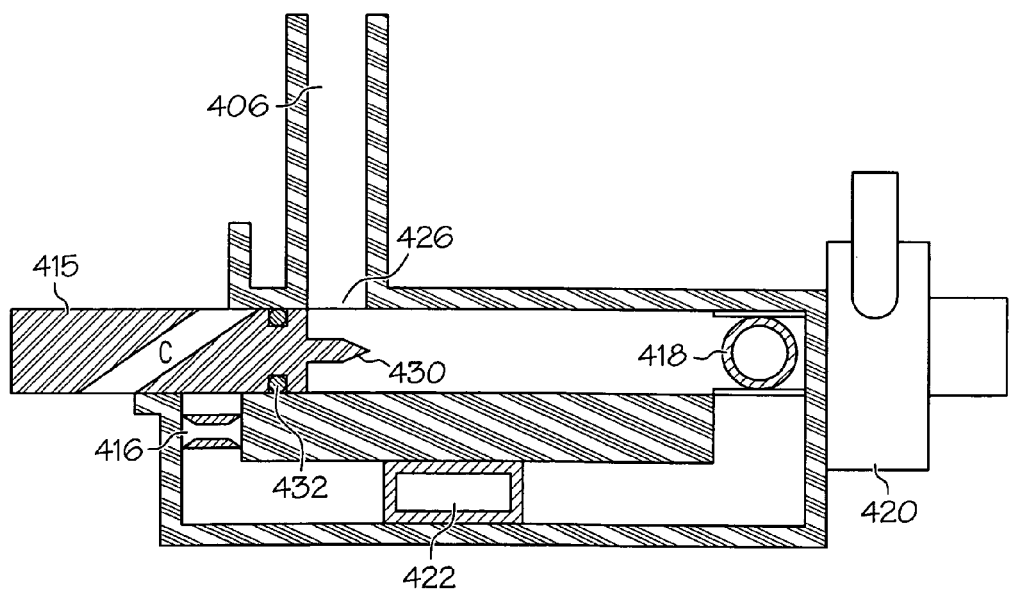
Figure 5A:
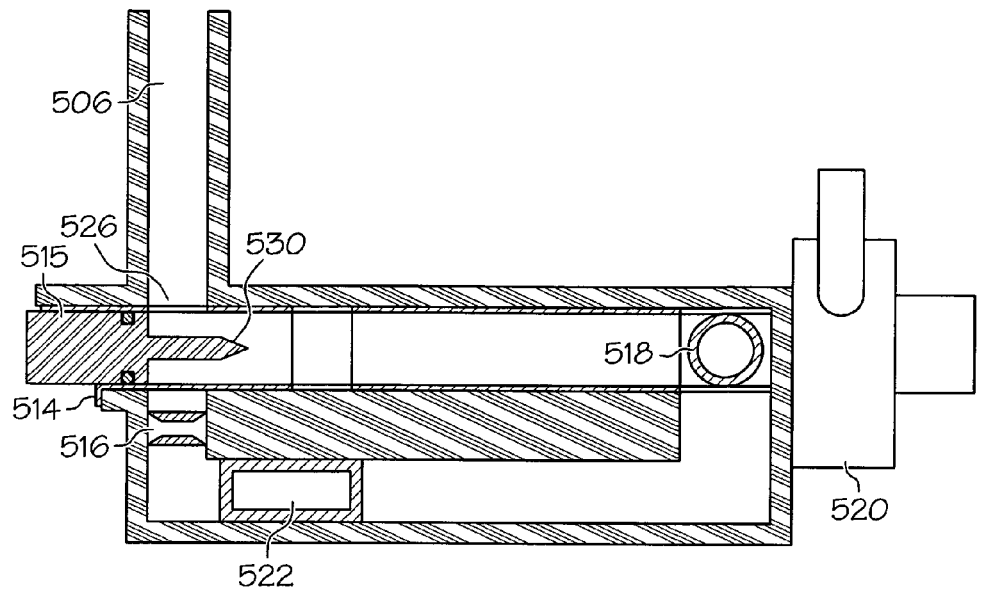
Figure 5B:
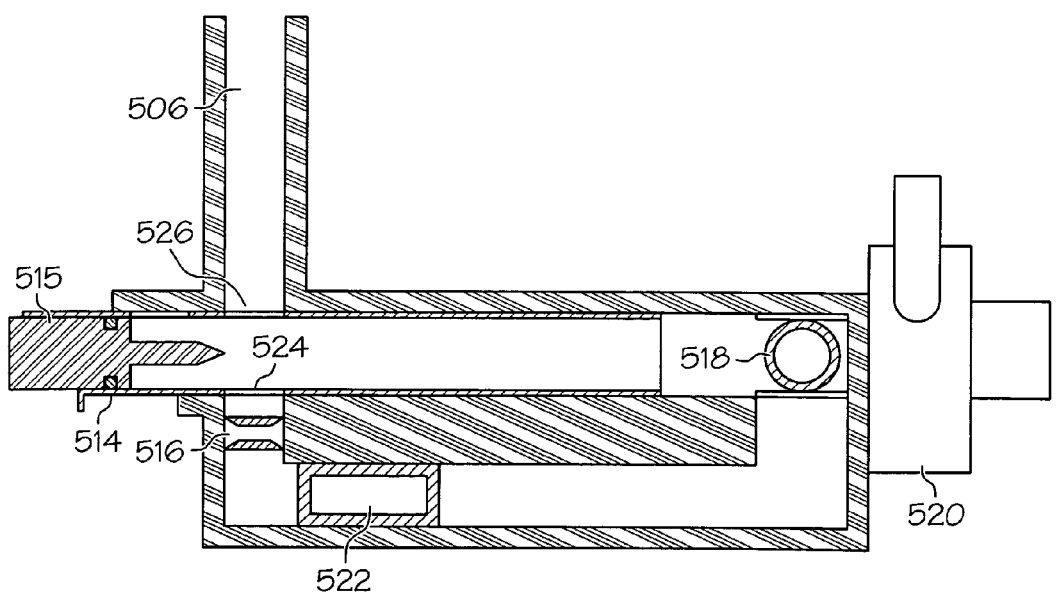

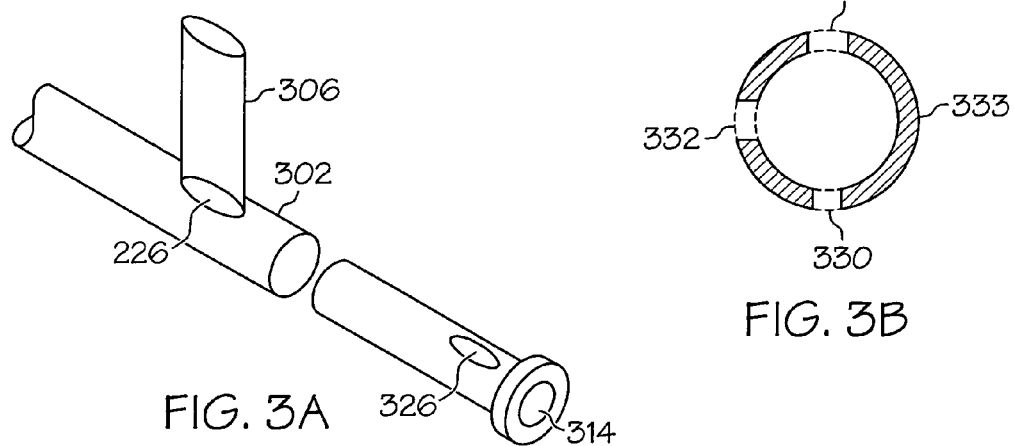
FIG. 3A
FIG. 3B
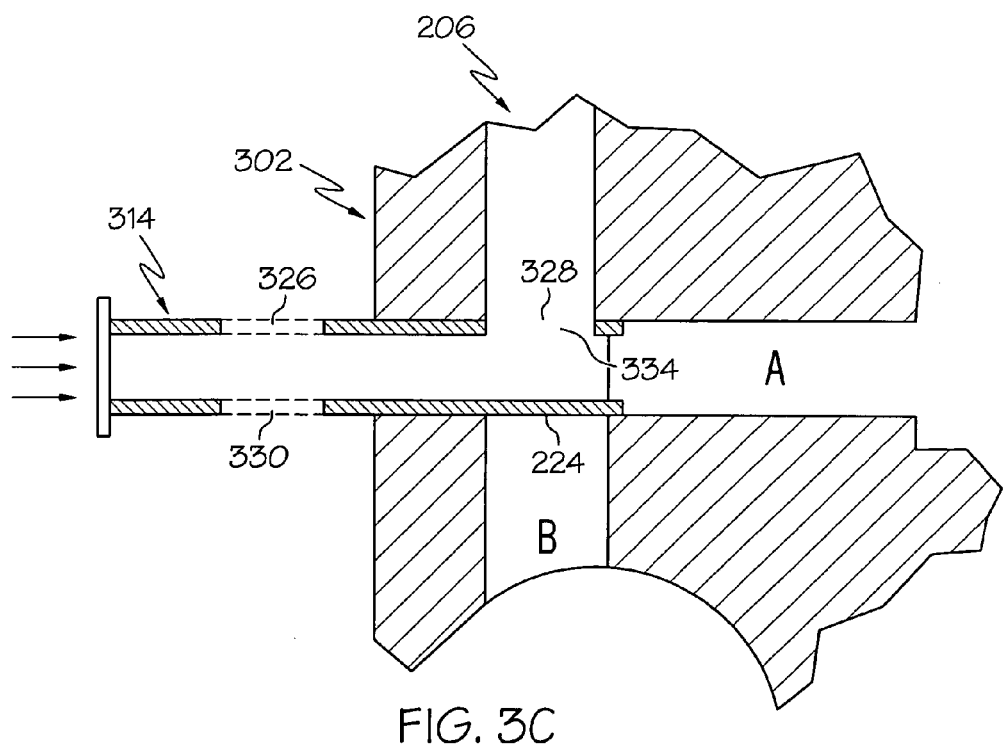
FIG. 3C

SYSTEMS AND METHODS FOR COLLECTION AND DETECTION OF PARTICULATES IN THE AIR

PRIORITY

This application claims priority of U.S. Provisional Application No. 60/964,983 filed Aug. 16, 2007.

FIELD

The present invention is in the field, of testing of air for biological, chemical, or nuclear particulates.

BACKGROUND

Walled Cyclones (WC) are mechanical apparatus utilized for the collection of aerosol particles for detection of trace levels of certain biological, explosive, chemical and nuclear materials. The principle of operation is to separate particulates present in the air based on size by taking advantage of the trajectory and flow dynamics of submicron particles as compared to macroscopic particles as the particles enter a rotational vortex in a pipe. The larger particles are acted on by inertial forces that push and separate the larger particulate to the inner wall of the cyclone while the smaller air gas molecules will be exhausted through the center of the pipe, exhausted out via a blower, fan or other air moving device. The inner surface of the cyclone is wetted, coated or consists of a material conducive to capturing particulates. Its surface is conditioned for the purpose of transporting or flushing the particulates into concentrated samples to be evaluated by biological, chemical, explosive or nuclear sensors, detectors, and identification apparatus.

FIG. 1 shows the basic architecture of a collection mechanism. The main body 102 is a pipe. The body is a molded or machined part that forms the interior and exterior surfaces of the cyclone. Within body 102 is a vortex finder 104. The vortex finder is a cone shaped protrusion at the bottom of inlet tube 106 that enhances the creation of a vortex in the cyclone body when air is flowing. An inlet tube 106 allows for inlet of air. The inlet tube provides a contoured interior surface that directs air flow from the entrance located on the upper portion into the cyclone body. An opening in body 102 allows the air to flow into the collection tube of body 102 through the opening. A wetting port 108 inserts a liquid that wets the air impaction region or cyclone body below the air inlet within body wall 102. In the wetting port a liquid may be injected into the cyclone for formation of a wetted surface along the cyclone wall for particulate collection. Air flows in the interior of the body 102 to an air outlet 110 where it is exhausted. The air outlet is interfaced to a blower or some other air suction device that generates the negative pressure that induces flow in the cyclone. While the air flows toward the exhaust, particulates flow along the wetted interior surface of body 102 toward a collection port 112. The particulates are collected at the collection port for future transport to sensors, detection devices and identifiers.

BRIEF DESCRIPTION OF THE DRAWINGS

Aspects of the invention will become apparent upon reading the following detailed description and upon reference to the accompanying drawings in which like references may indicate similar elements:

FIG. 1 depicts a basic wall cyclone apparatus

FIG. 2 depicts an embodiment for switching between a collection mode and a detection mode.

FIGS. 3A, B, and C depict an insert positionable within the collection tube.

FIGS. 3D and 3E depicts depict an insert wrapped with a heater element and insulation.

FIGS. 4A and 4B depict an embodiment for switching between a collection mode and a detection mode.

FIGS. 5A and 5B depict an embodiment for switching between a collection mode and a detection mode.

FIG. 6 depicts an embodiment with the inlet tube at an obtuse angle to the collection tube.

FIG. 7 depicts a wetting port.

FIGS. 8A and 8B depict an embodiment for switching between a collection mode and a detection mode.

FIGS. 9A and 9B depict an embodiment with a diaphragm to form a smoothly transitioning aperture between the air inlet and the collection tube.

FIGS. 10A, B and C depict an embodiment with a diaphragm to form a smoothly transitioning aperture between the air inlet and the collection tube.

FIGS. 11A and B depict an embodiment with an aperture that may be varied in size by rotation of the collection insert.

FIGS. 12A and B depict an embodiment with multiple air inlets.

FIG. 13 depicts a block diagram for adjusting airflow through the device in response to particle size.

FIG. 14 depicts various positions and sizes of a cap over the air inlet.

DETAILED DESCRIPTION OF EMBODIMENTS

The following is a detailed description of embodiments of the invention depicted in the accompanying drawings. The embodiments are in such detail as to clearly communicate the invention. However, the amount of detail offered is not intended to limit the anticipated variations of embodiments; but, on the contrary, the intention is to cover all modifications, equivalents, and alternatives falling within the spirit and scope of the present invention as defined by the appended claims. The detailed descriptions below are designed to make such embodiments obvious to a person of ordinary skill in the art.

Embodiments include systems and methods for collection and identification of particulates in the air. In one embodiment, two different path ways are provided: one for collection and one for detection. A removable collection insert positionable within a collection tube enables a user to switch between the collection mode and the detection mode. This embodiment captures both the physical mechanisms of switching the air flow paths as well as sequencing of controls and valves and regulation or changing the air flow rate in the different modes of operation. This and other embodiments are discussed herein.

FIG. 2 shows an embodiment for detection and/or collection of particulates from the air by a collection body 202. Air from the atmosphere flows inward through a collector inlet 206. Collector inlet tube 206 exhibits an interior surface that guides air into a collection insert 214 through an opening 226 such as a hole or slot that enables air to flow into collection insert 214. The device 200 is capable of operating in two modes. One mode is collection and another mode is detection. FIG. 2 shows operation in the detection mode. In the detection mode, air flow is through slot 226 and through detector inlet 224 into path B, through a concentrator 216, through detector 222 through a valve 218 and exhausting through a blower 220. Concentrator 216 receives the air from detector inlet 224 and forms it into two streams. One stream has larger particles and one stream has smaller particles. Detector 222 may comprise a laser optical system, a spectrometer, and/or or light, chemical or biological technologies that permit particles to pass through to be observed, quantified and discriminated. In the detection mode, valve 218 is positioned to allow air to pass from path B through the blower 220. The air flow rate can be varied to match the correct air flow for the detection device.

Thus, in the detection mode, air flows through a detector. In a collection mode, detector inlet 224 is closed. Air flows from collector inlet tube 206 through slot 226 into the interior of collection insert 214, passing through path A through valve 218 out through blower 220. Valve 218 may be an electromechanical device that in the detection mode allows air to pass from path B to blower 220, and in the collection mode allows air to pass from path A to blower 220. While air is passing through path A, particulates settle upon the wet walls of collection insert 214 and travel down the length of collection insert 214 toward a collection point near the end nearest the blower.

FIG. 3A shows a view of the collection insert 314 to be inserted into an interior cylinder (collection tube) of collection body 302. When the collection insert 314 is fully inserted and aligned, a slot 326 aligns with slot 226 at an end of a collection inlet tube 306. In one embodiment, another slot is in collection insert 314 that allows air to flow through to detector inlet 224. This occurs in the detection mode.

In one embodiment, a way to switch between the collection mode and the detection mode is to rotate collection insert 314. FIG. 3B shows a cross sectional view of the collection insert 314 for this embodiment. Collection insert 314 has three slots 326, 330 and 332 cut out of the wall. The length of each slot might be, for example, ⅛ of the total length of the collection insert. The length of the slots may be optimized through experimentation. Persons of skill in the art will readily recognize that instead of a slot, a hole may be employed or other opening of some shape. Two of the slots 326 and 330 are on opposite sides so that aligning one of them with slot 226 of the inlet 306, causes the slot on the opposite side to align with detector inlet 224. This places the device into the detection mode. When the third slot 332 in the wall of collection insert 314 is aligned with slot 226 of the inlet 306, the wall on the opposite side of slot 332 blocks the detector inlet 224. This places the device in the collection mode.

Another way to switch between collection mode and detection mode is to translate collection insert 314. In an embodiment shown in FIG. 3C, collection insert 314 is partially inserted into the collection tube of body 302 in a collection mode, and is fully inserted into the collection tube of body 302 in a detection mode. In a collection mode, collection insert 314 is only partially inserted so that a slot 334 in the wall of collection insert 314 lines up with slot 328 of collection inlet tube 306. On the opposite side of slot 334 is the wall of the collection insert 314 which blocks inlet to detector inlet 224. In this way, air flows through path A. Not shown in FIG. 3C is a vortex finder mounted near the end of collection insert 314. This helps to create a central vortex where particulates are pulled outward toward the interior wall of collection insert 314 and interior wall of body 302. In a detection mode, collection insert 314 is fully inserted so that slot 326 aligns with slot 328 and a slot 330 in collection insert 314 aligns with inlet 224. In this way, air flows through path B.

FIG. 3D shows a collection insert 314 wrapped by a heater 360 and then wrapped by insulation 362. The heater 360 focuses heat onto the collection insert where there is particle impaction. The insulation 362 avoids wasteful heating of the cyclone body. One desires the liquid in the collector to remain above freezing when the air entering the collector is cold. Wrapping collection insert 314 by heater 360 enables efficient localized heating. Prior art heating mechanisms disclose heating a substantial portion of the cyclone body, resulting in wasted energy. Embodiments that provide localized heating of the collection insert avoids this wasted energy.

FIG. 4A shows an embodiment with a vortex finder insert 415. The device is shown in the detection mode. In the detection mode, a path C is created in vortex finder insert 415. Path C is shown as a slant path but could also be a direct vertical path. To place the device in the detection mode, therefore, one need only position vortex finder insert 415 so that path C aligns with air inlet 406 and path B to allow the inlet air to pass through path C into path B through concentrator 416 through detector 422 through valve 418 and then out through blower 420. Concentrator 416 is positioned in the detection path below the air inlet and not in the air inlet, in contrast to some prior art detectors. FIG. 4B shows the device in the collection mode. Vortex finder insert 415 is positioned so that the vortex finder 430 is positioned just below the opening 426 to allow inlet air to flow into path A through valve 418 and out through blower 420. Note the O-ring 432 that provides a substantially water tight boundary between the two paths. Recall that liquid is sprayed into mix with the air flowing into air inlet 406. The vortex finder creates a vortex which causes particulate matter and liquid to collect on the interior wall of the body in path A. The liquid, with the particulate matter, flows in the direction of air flow along path A on the interior wall. The liquid reaches a collection port (not shown) positioned near valve 418 where the liquid with the particulate matter is collected.

FIG. 5A shows an embodiment with a collection insert 514 and a vortex finder insert 515. Vortex finder insert 515 inserts into the interior of collection insert 515. Collection insert 514 inserts into the collection tube of the body. FIG. 5A shows the device in the collection mode. Air flows from air inlet 506 through an opening 526 into path A moving past vortex finder 530 through valve 518 out through blower 520. Liquid with particulates flow along the interior of collection insert 515 toward a collection port (not shown) near valve 518. FIG. 5B shows the device in the detection mode. Air flows from inlet 506 through opening 526 through opening 524 into path B through concentrator 416 through detector 522 through valve 518 out through blower 520.

Traditionally cyclones are fabricated in single piece assemblies out of a uniform metallic material such as aluminum, stainless steel or plastic. In some embodiments, as described herein, fabrication of a wall cyclone assembly consists of a multiple part assembly. The assembly includes a molded, machined or rapid prototyped air inlet, a cyclone exterior body that forms a collection tube there within and that mates with a collection insert that forms the interior walls of the cyclone where particulate collection occurs. The collection insert allows the critical surfaces and surface finish for the impaction regions of the wall cyclone to be fabricated separately from the less critical and lower tolerance, parts of the assembly. The collection insert also permits the selection and tailoring of the material utilized for construction of the surfaces at the impaction region and those leading up to the collection port.

Separating the insert from the rest of the cyclone assembly permits a significant reduction in fabrication costs through a two step fabrication process: one for higher tolerance internal surfaces and a second for low tolerance exterior and aerodynamic inlet surfaces. Thus, one embodiment is a plastic molded part that may be mated with a metallic stainless steel or other metallic or plastic materials conducive to particle and living biological organisms transport that takes place in the insert. The insert can be made so that it is press fit into a through bore in the cyclone body. This press fit allows the collection insert to be removable from the side of the cyclone body opposite to the air outlet. Typically cyclonic collector interior surfaces should be cleaned to remove fibers and/or particulate buildup that can occur on the walls of the interior surfaces of the cyclone. During this servicing process it is desirable to observe and inspect the surfaces preceding the collection port for wear. Removability of the insert enables the insert and the surfaces where the liquid is collected to be easily inspected and serviced.

Thus, one embodiment is an air tester for testing for the presence of biological, chemical or nuclear particulates in the air. The embodiment comprises an air inlet to receive air and to channel it through a first opening in a wall of a collection tube. The embodiment further comprises a collection tube with a removable insert to collect liquid and particulates on the interior walls of the insert. The removable insert is positionable to align a first opening in a wall of the insert with the first opening in a wall of the collection tube to allow air to pass through the aligned openings. The air tester may further comprise, in a wall of the collection tube, a second opening to a detection path; and, in a wall of the insert, a second opening that, in a detection mode, aligns with the second opening in the wall of the collection tube when the first opening in the wall of the collection tube is aligned with the first opening in the wall of the insert, thus allowing air to pass through the insert to the detection path.

The embodiment may further comprise, in a wall of the insert, a third opening that can, in a collection mode, align with the first opening in the wall of the collection tube when the second openings are not aligned, to allow air to pass into and through the collection tube while air is sealed off to the detection path. In one embodiment, the insert rotates to a first position of alignment for the collection mode and rotates into a second position of alignment for the detection mode. In another embodiment, the insert translates to a first position of alignment for the collection mode and translates into a second position of alignment for the detection mode.

Another embodiment is a switchable air flow device for use in a detector of biological, chemical or nuclear particulates in the air. The embodiment comprises an air inlet connecting to a collection tube. The collection tube provides one path for air to flow for collection. A detection path provides a second path for air to flow for detection. The embodiment comprises an insert that is positionable in the collection tube. The insert has openings that can align with openings in the collection tube. In a first position, the insert allows air to flow from the air inlet through the insert to the detection path. In a second position, the insert allows air to flow from the air inlet to the collection tube while blocking the detection path when the insert is in a second position. The insert may also comprise a vortex finder positioned in proximity to the air inlet when the device in the second position. In one embodiment, the insert is positionable from the first position to the second position by rotation of the insert. In another embodiment, the insert is positionable from the first position to the second position by translation of the insert.

Figure 6:
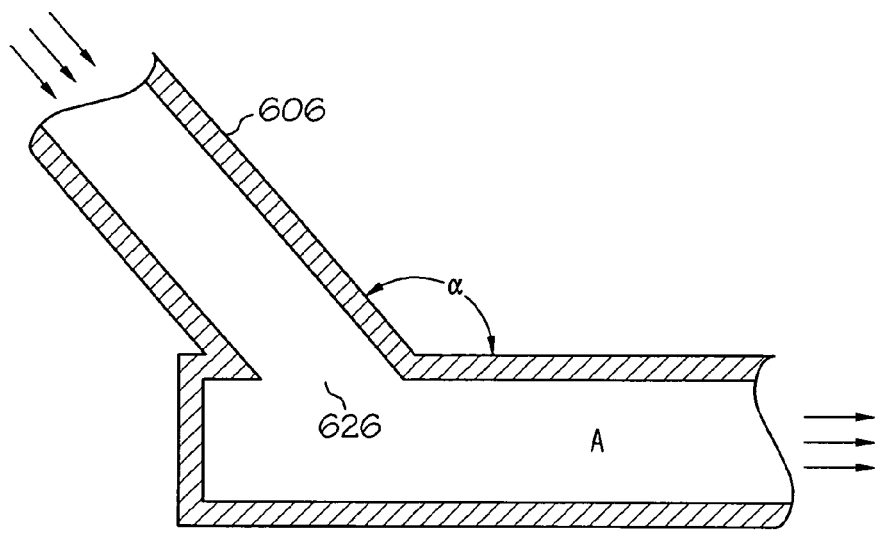

Illustrations of embodiments discussed heretofore show the air inlet being a tube that makes right angles with the direction (main axis) of the interior pipe forming path A (the collection tube). FIG. 6 shows an alternative embodiment wherein the air inlet path 606 forms an obtuse angle with the collection tube. Note that the air inlet tube may comprise interior walls that are shaped to optimize air flow into the device. Having the air inlet tube 606 make an obtuse angle with the collection tube reduces the pressure drop across opening 626. This allows use of a lower power blower and/or increased air flow rate. This configuration of the air inlet tube 606, making an obtuse angle with the collection tube, may be integrated into the devices of FIGS. 2, 3, 4 and 5 or other embodiments. Thus, in some embodiments, the air inlet is at an obtuse angle to a main axis of the collection tube. This also permits an adjustment of the size of particulate collected. So, by adjusting the angle, the size distribution of particles collected can be altered.

Figure 7:
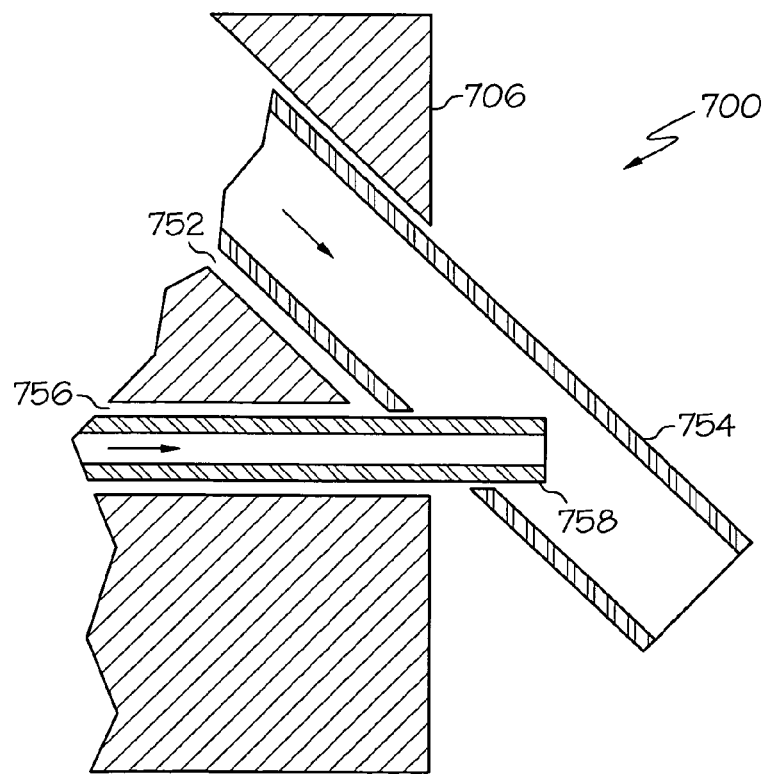

Not shown in FIGS. 2 through 6 is a wetting port in the wall of the air inlet 206, 306, 406, 506, 606. The wetting port allows for introduction of a liquid spray into the air inlet. In many applications, the liquid is water. In some applications, the liquid may be a solution comprising water and some chemical. FIG. 7 shows a wetting port 700 in a wall 706 of an air inlet. Passing through a first hole 752 in wall 706 is an air injector 754. Air injector 754 is a tube that passes air under pressure through injector 754 into the interior of the air inlet. Passing through a second hole 756 in wall 706 is a liquid injector 758. Liquid injector 758 is a tube that passes liquid under pressure through injector 758. The end of liquid injector 758 inserts into the interior of air injector 754. The air streaming through air injector 754 impacts the liquid flowing out of liquid injector 758 to cause a spray that exits air injector 754 and mixes with the air in the inlet. In past constructions of a wetting port, the air injector and the liquid injector are separate un-joined parts that must be placed in close proximity and in careful alignment. Joining these two parts together as shown in FIG. 7 eliminates this troublesome alignment problem. Thus, some embodiments comprise a wetting port comprising an air injector with an interior and a liquid injector; wherein an end of the liquid injector is inserted into the interior of the air injector.

Figure 8A:
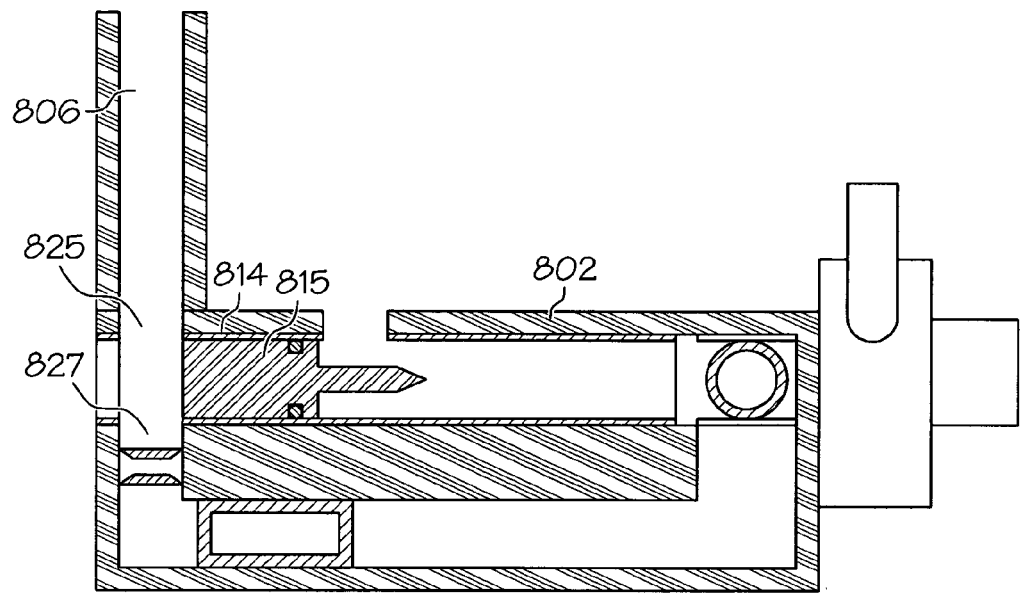
Figure 8B:
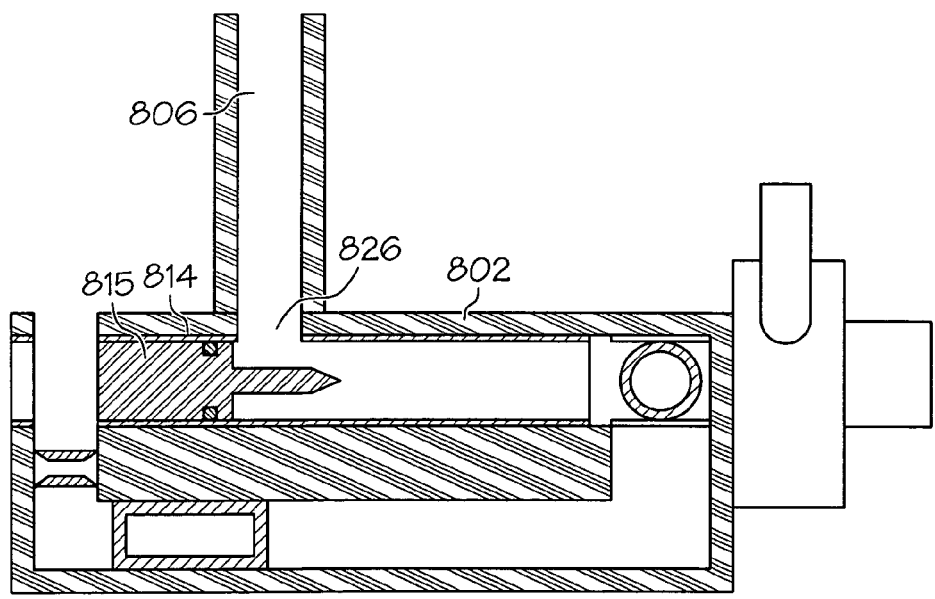

FIG. 8A and FIG. 8B show another embodiment of a cyclone collector/detector. In this embodiment, air inlet 806 is movable with respect to the cyclone body 802. In the position of FIG. 8A, the device operates in the detection mode. Air with particulates flow through air inlet 806 through aperture 825 through aperture 827 into air flow path B. The device is switchable to the collection mode of operation by moving air inlet 806 to a second position, as shown in FIG. B, so that the air inlet aligns with a third aperture 826 allowing air to flow through an aperture in the wall of collection insert 814. Air flows through aperture 826, past vortex finder insert 815 into air flow path A. In this embodiment, collection insert 814 and vortex finder insert 815 are removable for cleaning, inspection and servicing.

Thus, some embodiments comprise a collection tube providing a collection path and a detection tube providing a detection path with: an air inlet positionable with respect to the collection tube; wherein, in a first position, the air inlet aligns with apertures that allow air to flow through a detection path; and wherein, in a second position, the air inlet aligns with an aperture to allow air to flow through a collection path. An embodiment may further comprise a removable collection insert with a pair of apertures to allow air to flow through to the detection path and a third aperture to allow air to flow into the collection path while the detection path is blocked from the air inlet. An embodiment may further comprise a heater disposed about the collection insert to heat the collection insert. An embodiment may combine one, some, or all of the features described herein. Thus, an embodiment may have a positionable inlet wherein the inlet makes an obtuse angle with respect to the collection tube. This may be combined with a wetting port comprising an air injector with an interior and a liquid injector; wherein an end of the liquid injector is inserted into the interior of the air injector.

Figure 9A:
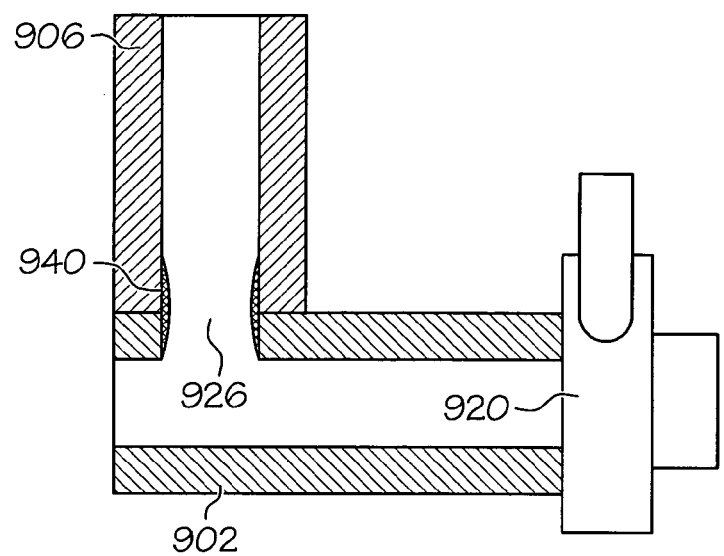
Figure 9B:
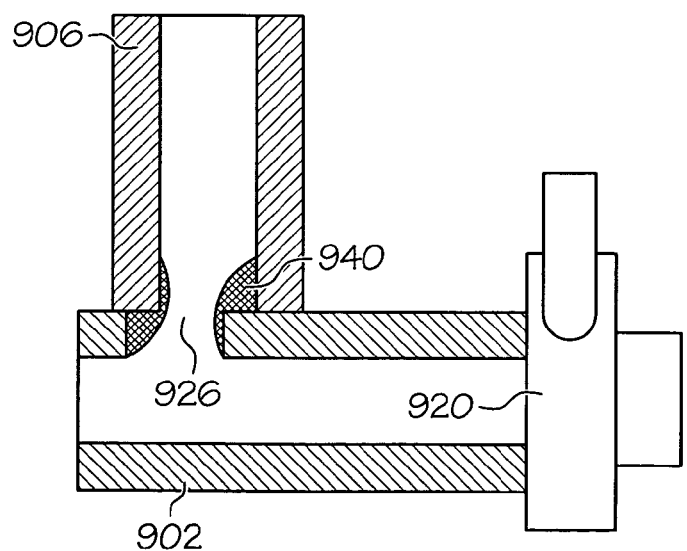

FIG. 9A and FIG. 9B show another embodiment for an air inlet 906 coupled through an aperture 926 to the interior of a cyclone body 902. A flexible diaphragm 940 is attached at a top to the interior wall of air inlet 906 and is attached at a bottom to the cyclone body. Air flows through opening 926 through the interior of the cyclone body 902 out through blower 920. In this embodiment, the air inlet 906 is movable relative to the cyclone body along the axis of the cyclone. In one position of air inlet 906, a wide opening 926 is provided, but in another position of air inlet 906, the diaphragm 940 deforms to provide a much narrower opening 926. A narrow opening will, for the same flow rate, cause air to flow through the opening 926 at a higher velocity, resulting in discrimination of smaller particles. Note that this embodiment can be combined with embodiments described above to provide a cyclone with a plurality of features described herein. Note also, that the aperture formed by the diaphragm makes a smooth transition from the air inlet to the collection tube. Note further that in some embodiments the opening 926 is varied by inflating or deflating an inflatable diaphragm 940.

Figure 10A:
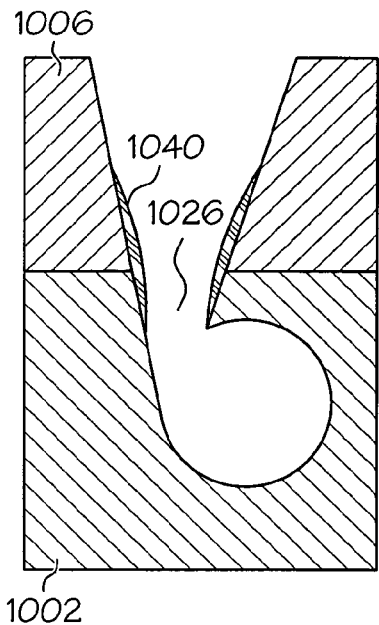
Figure 10B:
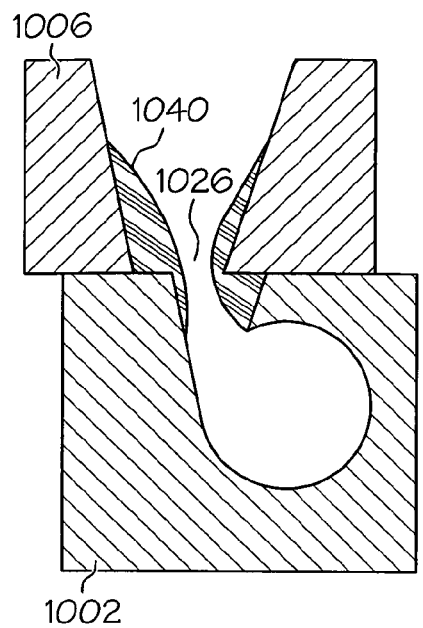
Figure 10C:
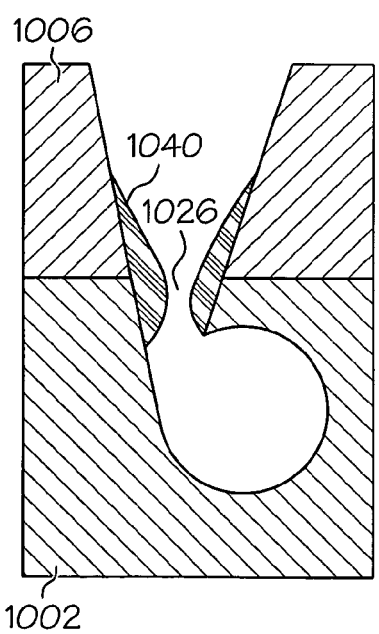

FIG. 10A and FIG. 10B show an alternative embodiment wherein the air inlet 1006 moves laterally with respect to the cyclone body 1002, rather than longitudinally as shown in FIGS. 9A and 9B. The flexible diaphragm 1040 is attached to the air inlet 1006 interior wall and to the cyclone body 1002. In one position, the aperture 1026 of the diaphragm 1040 is opened to a maximum extent (FIG. 10A). In another position—laterally, with respect to cyclone body 1002—the aperture 1026 is narrowed (FIG. 10B). Note that in FIGS. 9 and 10, the diaphragm produces an interior wall that is smooth for a smooth transition between the two parts, thereby avoiding the generation of turbulence at the aperture and reducing settlement of particulates at or near the aperture. FIG. 10C shows yet another alternative for providing a smooth transition across the aperture. In this embodiment, flexible diaphragm 1040 is deformable by way of air provided by an air pump (not shown). Thus, aperture 1026 can be made small or large without movement of any parts other than the diaphragm 1040. By variably inflating the diaphragm, one can obtain good control over the size of the aperture 1026.

Thus, some embodiments have a flexible diaphragm to couple air from the air inlet to the collection tube. One embodiment is an air flow device with a collection tube providing a collection path. Coupled to the collection tube, is an air inlet to receive air from the exterior of the device and to transmit air to the interior of the collection tube. A flexible diaphragm attached at one side to an interior wall of the air inlet and attached at another side to the collection tube forms a smoothly transitioning aperture. In one embodiment, the flexible diaphragm is inflatable to vary the size of an aperture formed by the diaphragm. In another embodiment, the air inlet moves with respect to the collection tube to flex the diaphragm to vary the size of an aperture formed by the diaphragm. The air inlet may move laterally with respect to the collection tube in one embodiment or may move longitudinally with respect to the collection tube in another embodiment. In some embodiments, the diaphragm attaches to a collection insert of the collection tube.

Figure 11A:
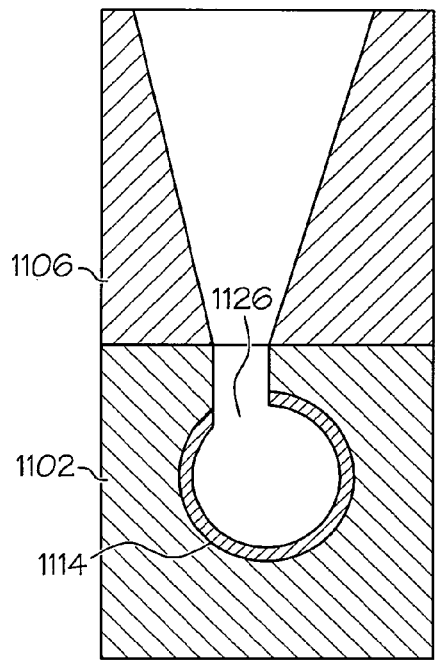
Figure 11B:
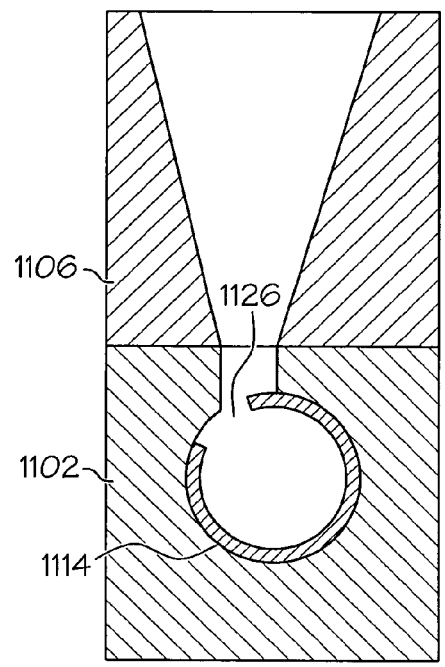

FIG. 11A and FIG. 11B show yet another way to controllably restrict the aperture between the air inlet 1106 and cyclone body 1102 by changing the size of the aperture 1126. The size of the aperture 1126 is varied by a small rotation of collection insert 1114. This embodiment may be combined with a diaphragm to smooth the transition across aperture 1126. By a small rotation of the collection insert, particles of different sizes can be collected. Thus, in some embodiments, an aperture between the air inlet and the collection tube may be varied in size by a relatively small rotation of a collection insert inserted into the collection tube interior.

Figure 12A:
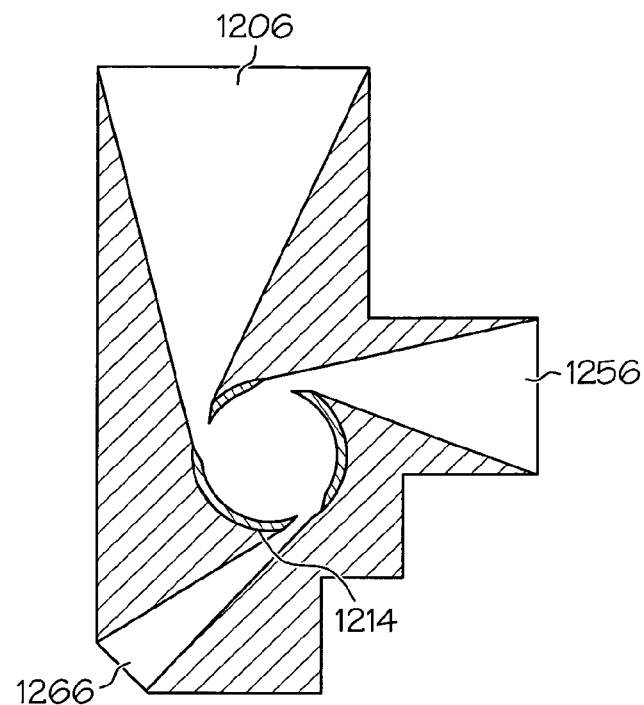
Figure 12B:
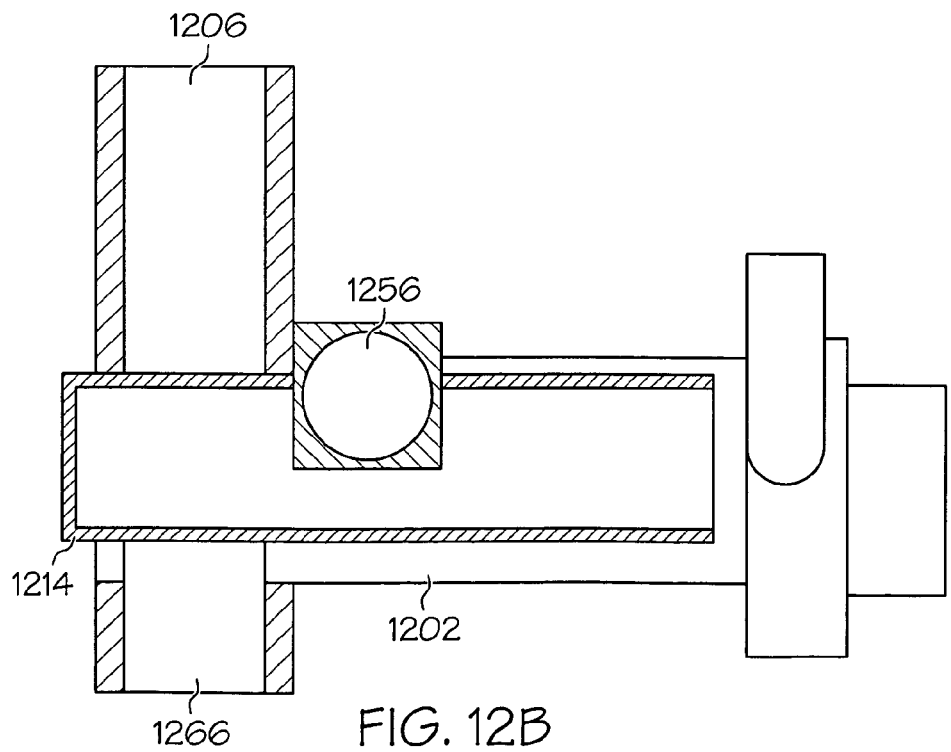

FIG. 12A and FIG. 12B show a cyclone with multiple air inlets 1206, 1256, and 1266. Each air inlet is connected by an aperture in collection insert 1214 to the interior of the cyclone body 1202. Each aperture in collection insert 1214 may line up with an air inlet. The apertures may be so arranged that only one inlet is open at a time, or so that a plurality of inlets are open at a time as shown in FIG. 12A. Thus, the atmosphere can be collected through different inlets, each with its own air flow rate. The air flow rate may be determined by the size of the aperture. This means that different particles sizes can be collected. FIG. 12B shows that air inlets may be placed at different positions along the length of the collection tube 1202. In FIG. 12B, two air inlets 1206 and 1266 are equally displaced along the length of collection tube 1202. A third air inlet 1256 is displaced further along the length of collection tube 1202. Thus, in some embodiments, a plurality of air inlets may be disposed angularly about the circumference of the collection tube, or disposed along the length of the collection tube, or both. This enables collection of different size particles at different areas along the length of the collection tube. In some embodiments, one or more air inlets may be selected by rotating the collection insert 1214 or translating the collection insert 1214 or by a combination of rotation and translation. A further advantage of using multiple air inlets simultaneously is that larger volumes of air can be sampled for particulates.

Thus, some embodiments comprise a collection tube with a plurality of air inlets to receive air from the exterior of the device and to transmit air to the interior of the collection tube. An embodiment may further comprise a collection insert with apertures that may align with one or more air inlets at a time. In one embodiment, some air inlets are displaced from each other longitudinally along the length of the collection tube. In another embodiment, or in the same embodiment, some air inlets are displaced angularly from each other about the circumference of the collection tube. Moreover, in some embodiments, some air inlets are connected to the collection tube through apertures of different sizes.

Figure 13:
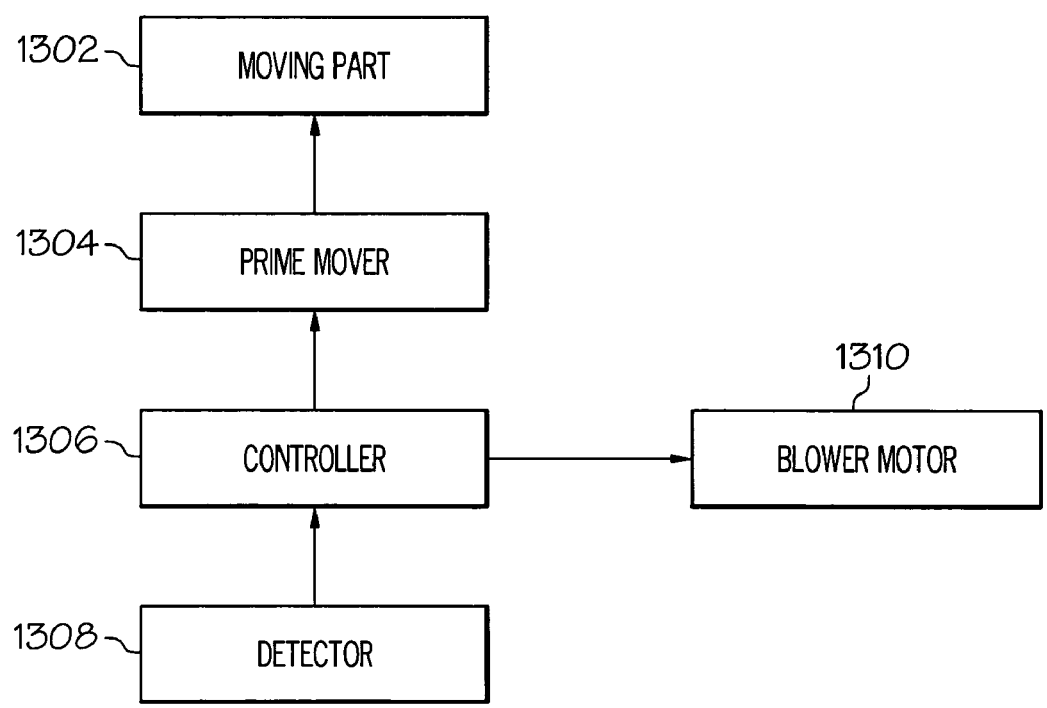
Figure 14A:
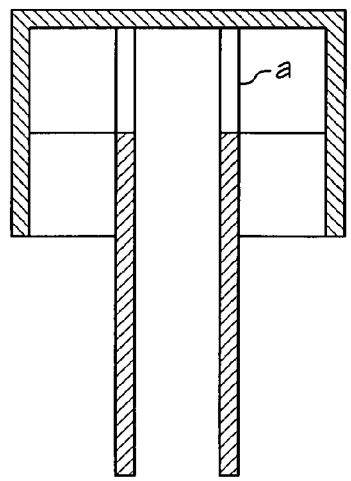
Figure 14B:
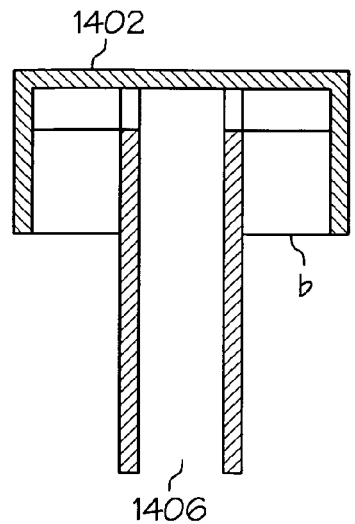
Figure 14C:
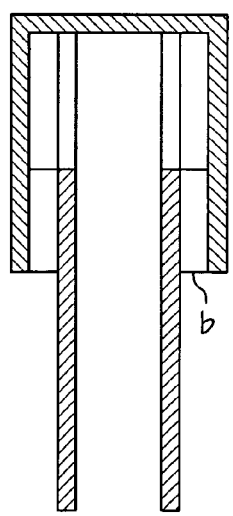

FIG. 13 shows a functional block diagram for automatically adjusting the size of an inlet or adjusting the speed of a blower motor in response to a detected particle size. Detector 1308 is positioned as shown in any one of FIG. 2, 4, 5 or 8 or otherwise positioned in a path to receive and detect particles. Detector 1308 can detect the size of particles it receives or that pass through or by it. In one embodiment, detector 1308 comprises a laser light that is deflected by particles. The bigger the particle causing the deflection, the signal seen by the detector indicates the specific target particle size. Thus, detector 1308 is responsive to particle size. Further, detector 1308 produces a signal responsive to particle size.

A controller 1306 receives a signal from detector 1308 that is responsive to particle size. controller 1306 is programmed to produce a signal responsive to the signal from detector 1308 that drives a prime mover, such as a stepper motor, 1304. Generally, prime mover 1304 is an electromechanical device that transfers an electrical signal to motion. Device 1304 drives a movable part of the collection/detection apparatus to vary the size of an inlet through which the particles pass. In addition, or in the alternative, controller 1306 adjusts the speed of a blower motor 1310 that causes a change in the air flow rate through the apparatus. The change in air flow rate allows for adjustment in particle size collection.

In one embodiment, controller 1306 comprises a look up table or other method to develop an output signal to drive motor 1304 in response to an input signal responsive to particle size. Motor 1304 drives a moving part of the apparatus to vary the size of an inlet through which the particles pass. For example, referring to FIG. 2, the motor could drive the collection insert 314 either translationally in one embodiment or rotationally in another embodiment to very the size of the inlet through which the particles pass. As another example, referring to FIG. 9 or 10, the air inlet 906 or 1006 can be moved translationally to vary the size of the inlet. In the embodiment of FIG. 11, as yet another example, the collection insert 1114 can be rotated to vary inlet size.

Thus, in response to a particle stream flowing through detector 1308, the detector outputs a signal responsive to and indicative of the size of particles detected. The controller receives this signal and, in response, outputs a signal to either the prime mover 1304 or the blower motor 1310 or both. The signal output of the microcontroller may be calculated or calibrated to cause air to pass through an inlet of a size selected to optimize collection of particles of a particular size. For example, if the detector detects a particle size of 10 microns, the system may be calibrated to create an air inlet that increases the collection of particles of this size. This may be done automatically. Generally, the smaller the opening of the inlet, the higher the velocity of air flow there through, and the smaller the particles being collected. Conversely, a larger opening reduces velocity resulting in larger particles being collected.

FIG. 14 shows another aspect of some embodiments which have a cap 1402 over the air inlet 1406 of the apparatus. In some embodiments, the cap 1402 is movable with respect to inlet 1406. Thus, in FIG. 14A the cap is raised so that height a is tall. In FIG. 14B the cap is lowered. When the cap is raised, velocity into the inlet decreases and larger particles are collected. Conversely, when the cap is lowered, velocity increases and smaller particles are collected. In some embodiments, a width of the cap may be varied to adjustably select particle size. This can be seen by comparing b of FIGS. 14B and 14C. In some embodiments, therefore, the cap or the inlet may be moved or adjusted with respect to the other to change the volume between the cap and the inlet to adjustably select particle size. In some embodiments, the cap is adjustable by prime mover 1304 which is ultimately responsive to the signal from the detector indicative of particle size. In some embodiments, the cap or the inlet is adjustable by rotating the cap or inlet to vary the velocity of particles being aspirated into the inlet. Note finally, that in some embodiments the detector is in a path separate from the collection tube. In some embodiments, the detection path may be within the collection tube.

The present invention and some of its advantages have been described in detail for some embodiments. It should be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. One of ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. An air tester for testing for the presence of biological, explosive, chemical or nuclear particulates in the air, comprising:

a collection tube;

an air inlet to receive air and to channel the air through a first opening in a wall of the collection tube; and a removable insert insertable into the collection tube and having interior walls, the removable insert collecting liquid and particulates on the interior walls of the insert; the removable insert being positionable to align a first opening in a wall of the insert with the first opening in a wall of the collection tube to allow air to pass through the aligned openings, the removable insert being substantially concentric with the collection tube;

a wall of the collection tube having a second opening to a detection path;

a wall of the insert having a third opening that, in a detection mode aligns with the second opening in the wall of the collection tube when the first opening in the wall of the collection tube is aligned with the first opening in the wall of the insert, to allow air to pass through the insert to the detection path.

2. The air tester of claim 1, further comprising:

in a wall of the insert, a third opening that can, in a collection mode, align with the first opening in the wall of the collection tube when the second openings are not aligned, to allow air to pass into and through the collection tube while air is sealed off to the detection path.

3. The air tester of claim 2, wherein the insert rotates to a first position of alignment for the collection mode and rotates into a second position of alignment for the detection mode.

4. The tester of claim 1, wherein the alignment between the first opening in the wall of the collection tube and the first opening in the wall of the insert is electro-mechanically adjustable in response to a signal from a detector in the detection path.

5. The tester of claim 4, wherein the signal from the detector is a function of a size of particles detected by the detector.

6. The tester of claim 1, wherein a path of the air inlet is at an obtuse angle to a main axis of the collection tube.

7. The tester of claim 1, further comprising a wetting port comprising an air injector with an interior and a liquid injector; wherein an end of the liquid injector is inserted into the interior of the air injector.

8. A switchable air flow device for use in a detector/collector of biological, explosive, chemical or nuclear particulates in the air, the switchable air flow device comprising:

a collection tube providing a first path for air to flow;

an air inlet connecting to the collection tube;

a detection path providing a second path for air to flow; and an insert positionable within the collection tube, with openings therein, to allow air to flow from the air inlet through the insert to the detection path when the insert is rotated to be in a first position and to allow air to flow from the air inlet to the collection tube while blocking the detection path when the insert is rotated to be in a second position, the insert comprising a vortex finder.

9. The device of claim 8, wherein the insert is removable from the collection tube.

10. The device of claim 8, wherein a path of the air inlet is at an obtuse angle to a main axis of the collection tube.

11. The device of claim 8, wherein the insert is positionable from the first position to the second position by rotation of the insert.

12. The device of claim 8, wherein the insert has a heating layer.

13. The device of claim 12, wherein the insert has an insulation layer outside the heating layer.

14. The device of claim 8, wherein the second position is determined in response to a signal from a detector in the detection path.

15. The device of claim 8, further comprising an adjustable cap over an end of the air inlet to vary the flow rate of air in the inlet.

16. An air flow device for use in a collector of biological, explosive, chemical or nuclear particulates in the air, the air flow device comprising:
a collection tube having an interior and a first aperture, the collection tube providing a collection path;
coupled to the collection tube, an air inlet to receive air from an exterior of the device and to transmit air to the interior of the collection tube, the collection tube being cylindrical and rotatable about a longitudinal axis to align the first aperture in the collection tube with the air inlet
a detection path having an aperture align-able with a second aperture of the collection tube to enable air to pass through the second collection tube aperture and the detection path aperture into the detection path.

17. The device of claim 16, wherein a flow rate through at least one the inlet is adjustable.

18. A particle detection and collection device, comprising:
a collection path and a detection path, the collection path bypassing the detection path and the detection path bypassing the collection path;
a detector in the detection path to detect particles and to produce a signal responsive to particle size; and
circuitry to produce a signal to an electromechanical device to cause motion to vary the velocity of air flowing through an inlet to the collection path in response to the signal from the detector;
an electromechanical device to vary a position of a moveable part of the device to vary the velocity of air flowing through the inlet in response to the signal from the detector.

19. The device of claim 18, wherein the moveable part is a collection insert inserted into the collection path.

20. The device of claim 18, further comprising a cap over an end of the inlet, wherein adjusting a relative position between the cap and the inlet adjusts a velocity of air received by the inlet.

* * * * *

UNITED STATES PATENT AND TRADEMARK OFFICE
CERTIFICATE OF CORRECTION

PATENT NO. : 8,205,512 B1
APPLICATION NO. : 12/228899
DATED : June 26, 2012
INVENTOR(S) : Jeffrey Charles Michalski, Matthew Tant Richardson and Michael Joseph Foley Page 1 of 1

It is certified that error appears in the above-identified patent and that said Letters Patent is hereby corrected as shown below:

In the Claims:
In Column 12, lines 1-2, Claim 17, delete "at least one".

Signed and Sealed this
Fourth Day of September, 2012

David J. Kappos
*Director of the United States Patent and Trademark Office*